United States Patent
Iveson et al.

(10) Patent No.: US 9,533,059 B2
(45) Date of Patent: Jan. 3, 2017

(54) PEPTIDE RADIOTRACER COMPOSITIONS

(75) Inventors: Peter Brian Iveson, Buckinghamshire (GB); Rajiv Bhalla, Buckinghamshire (GB); Bard Indrevall, Oslo (NO); Gareth Getvoldsen, Buckinghamshire (GB)

(73) Assignee: GE HEALTHCARE LIMITED, Buckinghampshire (GB)

( * ) Notice: Subject to any disclaimer, the term of this patent is extended or adjusted under 35 U.S.C. 154(b) by 97 days.

(21) Appl. No.: 13/816,589

(22) PCT Filed: Aug. 11, 2011

(86) PCT No.: PCT/EP2011/063890
§ 371 (c)(1),
(2), (4) Date: Feb. 12, 2013

(87) PCT Pub. No.: WO2012/022676
PCT Pub. Date: Feb. 23, 2012

(65) Prior Publication Data
US 2013/0149241 A1    Jun. 13, 2013

(30) Foreign Application Priority Data

Aug. 18, 2010  (GB) .................................. 1013808.9

(51) Int. Cl.
| A61K 51/08 | (2006.01) |
| A61K 38/16 | (2006.01) |
| A61K 38/18 | (2006.01) |
| A61K 49/00 | (2006.01) |
| C07K 7/64 | (2006.01) |

(52) U.S. Cl.
CPC ............. *A61K 49/00* (2013.01); *A61K 51/088* (2013.01); *C07K 7/64* (2013.01); *A61K 38/16* (2013.01); *A61K 38/1833* (2013.01)

(58) Field of Classification Search
None
See application file for complete search history.

(56) References Cited

U.S. PATENT DOCUMENTS

| 5,961,955 | A | * | 10/1999 | Shochat et al. ............. 424/1.69 |
| 8,529,874 | B2 | | 9/2013 | Johannesen et al. |
| 8,557,776 | B2 | | 10/2013 | Lehmann et al. |
| 2010/0068150 | A1 | | 3/2010 | Bogyo et al. |

FOREIGN PATENT DOCUMENTS

| JP | 2009-542689 A | 12/2009 |
| JP | 2010520229 A | 6/2010 |
| JP | 2010526859 A | 8/2010 |
| JP | 5309141 B2 | 10/2013 |
| JP | 5341757 B2 | 11/2013 |
| WO | 2004/078778 | 9/2004 |
| WO | 2004/080492 | 9/2004 |
| WO | 2006/030291 | 3/2006 |
| WO | WO 2006/030291 A2 | 3/2006 |
| WO | 2008/072976 | 6/2008 |
| WO | 2008/139207 | 11/2008 |
| WO | WO 2008/139207 A2 | 11/2008 |
| WO | 2009/016180 | 2/2009 |
| WO | 2009016181 | 2/2009 |
| WO | WO 2009/016180 A2 | 2/2009 |
| WO | WO20090161180 A2 | 2/2009 |
| WO | WO2009-027706 A2 | 3/2009 |
| WO | WO 2009106566 A2 * | 9/2009 |

OTHER PUBLICATIONS

Kilbourn et al., "Fluorine-18 Labeling of Proteins", J Nucl Med, 1987, pp. 462-470.*
Poethko et al., "Two-Step Methodology for High-Yield Routine Radiohalogenation of Peptides: 18F-Labeled RGD and Octreotide Analogs", J Nucl Med, 2004, pp. 892-902.*
Poethko Journal of Nuclear Medicine, Society of Nuclear Medicine, Reston, VA, vol. 45, No. 5, May 1, 2004, pp. 892-902 "Two-Step Methodology for High-Yield Routine Radiohalogenation of Peptide: 18F-Labled RGD and Octreotide Analogs".
PCT/EP2011/063890 ISRWO Dated Dec. 19, 2011.
Great Britain 1013808.9 Search Report Dated Dec. 15, 2010.
Flavell Journal American Chemical Society, 2008, vol. 1330, pp. 9106-9112 "Site-Specific 18F-Labeling of the Protein Hormone Leptin Using a General Two-Step Ligation Procedure".
Office Action (translation) issued in Chile Application No. 483-2013 (Dec. 17, 2015).
Japanese Office Action issued May 17, 2016 in corresponding JP Appl. No. 2013-524419. (English Translation attached).

* cited by examiner

*Primary Examiner* — Lianko Garyu
(74) *Attorney, Agent, or Firm* — Wood IP LLC

(57) ABSTRACT

The present invention relates to imaging agent compositions comprising radiolabelled c-Met binding peptides suitable for positron emission tomography (PET) imaging in vivo. The c-Met binding peptides are labelled with the radioisotope $^{18}F$. Also disclosed are pharmaceutical compositions, methods of preparation of the agents and compositions, plus methods of in vivo imaging using the compositions, especially for use in the management of cancer.

16 Claims, 1 Drawing Sheet

FastLab™ Cassette Configuration for Example 11.
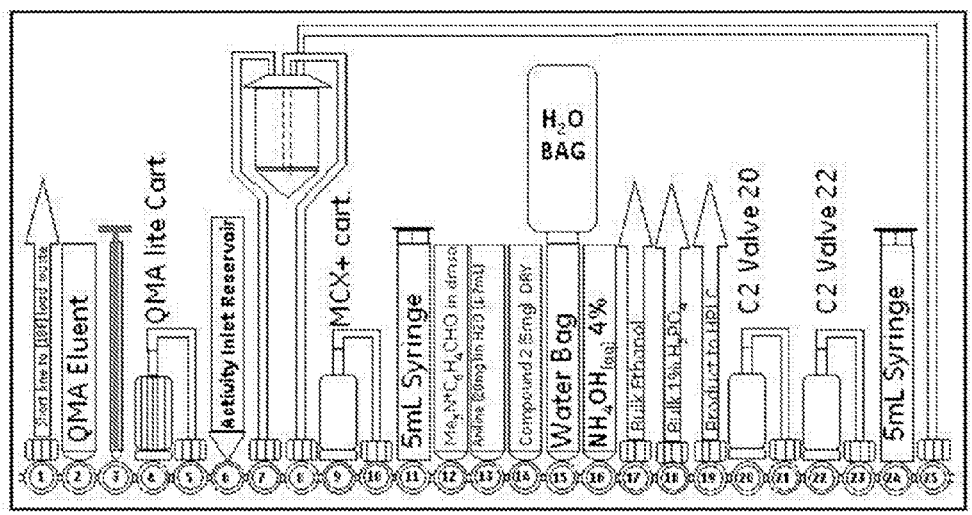
where:
QMA = quaternary methyl ammonium water treatment SPE cartridge;
MCX+ = mixed cation exchange SPE cartridge;
C2 = low hydrophobicity silica-based SPE cartridge.

PEPTIDE RADIOTRACER COMPOSITIONS

CROSS REFERENCE TO RELATED APPLICATIONS

This application is a filing under 35 U.S.C. 371 of international application number PCT/EP2011/063890, filed Aug. 11, 2011, which claims priority to Great Britain application number 1013808.9 filed Aug. 18, 2010, the entire disclosure of which is hereby incorporated by reference.

FIELD OF THE INVENTION

The present invention relates to imaging agent compositions comprising radiolabelled c-Met binding peptides suitable for positron emission tomography (PET) imaging in vivo. The c-Met binding peptides are labelled with the radioisotope $^{18}$F. Also disclosed are pharmaceutical compositions, methods of preparation of the agents and compositions, plus methods of in vivo imaging using the compositions, especially for use in the diagnosis of cancer.

BACKGROUND TO THE INVENTION

Hepatocyte growth factor (HGF), also known as scatter factor (SF), is a growth factor which is involved in various physiological processes, such as wound healing and angiogenesis. The high affinity interaction of HGF interaction with its receptor (c-Met) is implicated in tumour growth, invasion and metastasis.

Knudsen et al have reviewed the role of HGF and c-Met in prostate cancer, with possible implications for imaging and therapy [Adv. Cancer Res., 91, 31-67 (2004)]. Labelled anti-met antibodies for diagnosis and therapy are described in WO 03/057155.

c-Met has been shown to be involved in tumour growth, invasion and metastasis in many human cancers of epithelial origin. c-Met is expressed by most carcinomas and its elevated expression relative to normal tissue has been detected in cancers of: lung, breast, colorectal, pancreatic, head and neck, gastric, hepatocellular, ovarian, renal, glioma, melanoma and a number of sarcomas. In colorectal carcinoma (CRC), over-expression of c-Met has been detected in dysplastic aberrant crypt foci, the earliest pre-neoplastic lesions of the disease. In head and neck squamous cell cancer, c-Met is reportedly expressed or overexpressed in roughly 80% of primary tumours. In prostate cancer metastasis to bone, c-Met was reported overexpressed in over 80% of bone metastasis.

Under normal conditions, c-Met is expressed on epithelial cells and activated in a paracrine fashion, by mesenchymally derived HGF. The activation of c-Met in normal cells is a transient event and is tightly regulated. In tumour cells, however, c-Met can be constitutively active. In cancer, aberrant c-Met stimulation can be achieved through c-Met amplification/over-expression, activating c-Met mutations (e.g. structural alterations) and acquisition of autonomous growth control through creation of autocrine signalling loops. In addition, a defective down-regulation of the c-Met receptor will also contribute to aberrant c-Met expression in the cell membrane. While the over-expression of c-Met is HGF dependent (autocrine/paracrine), structural alterations caused by mutations are HGF independent (e.g. loss of extracellular domain).

WO 2004/078778 discloses polypeptides or multimeric peptide constructs which bind c-Met or a complex comprising c-Met and HGF. Approximately 10 different structural classes of peptide are described. WO 2004/078778 discloses that the peptides can be labelled with a detectable label for in vitro and in vivo applications, or with a drug for therapeutic applications. The detectable label can be: an enzyme, a fluorescent compound, an optical dye, a paramagnetic metal ion, an ultrasound contrast agent or a radionuclide. Preferred labels of WO 2004/078778 are stated to be radioactive or paramagnetic, and most preferably comprise a metal which is chelated by a metal chelator. WO 2004/078778 states that the radionuclides therein can be selected from: $^{18}$F, $^{124}$I, $^{125}$I, $^{131}$I, $^{123}$I, $^{77}$Br, $^{76}$Br, $^{99m}$Tc, $^{51}$Cr, $^{67}$Ga, $^{47}$Sc, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{203}$Pb, $^{211}$Bi, $^{212}$Bi, $^{213}$Bi, $^{214}$Bi, $^{105}$Rb, $^{109}$Pd, $^{117m}$Su, $^{149}$Pm, $^{161}$Tb, $^{177}$Lu, $^{198}$Au and $^{199}$Au. WO 2004/078778 states (page 62) that the preferred radionuclides for diagnostic purposes are: $^{64}$Cu, $^{67}$Ga, $^{68}$Ga, $^{99m}$Tc and $^{111}$In, with $^{99m}$Tc being particularly preferred.

WO 2008/139207 discloses c-Met binding cyclic peptides of 17 to 30 amino acids which are labelled with an optical reporter imaging moiety suitable for imaging the mammalian body in vivo using light of green to near-infrared wavelength 600-1200 nm. The c-Met binding peptides comprise the amino acid sequence SEQ ID NO: 1:

Cys$^a$-X$^1$-Cys$^c$-X$^2$-Gly-Pro-Pro-X$^3$-Phe-Glu-Cys$^d$-Trp-Cys$^b$-Tyr-X$^4$-X$^5$-X$^6$;

wherein X$^1$ is Asn, H is or Tyr;
X$^2$ is Gly, Ser, Thr or Asn;
X$^3$ is Thr or Arg;
X$^4$ is Ala, Asp, Glu, Gly or Ser;
X$^5$ is Ser or Thr;
X$^6$ is Asp or Glu;
and Cys$^{a-d}$ are each cysteine residues such that residues a and b as well as c and d are cyclised to form two separate disulfide bonds. The optical reporter of WO 2008/139207 is preferably a cyanine dye.

WO 2009/016180 discloses c-Met binding cyclic peptides analogous to those of WO 2008/139207, wherein the optical reporter is a benzopyrylium dye. The agents of WO 2008/139207 and WO 2009/016180 are stated to be useful for in vitro and in vivo optical applications, especially optical imaging in vivo of the human body. Optical imaging of colorectal cancer is a preferred application.

SUMMARY OF THE INVENTION

The present invention relates to imaging agent compositions comprising $^{18}$F-radiolabelled c-Met binding peptides suitable for positron emission tomography (PET) imaging in vivo. The c-Met binding peptides are labelled via a lysine (Lys) residue.

The imaging agent compositions preferably suppress the level of unlabelled c-Met binding cyclic peptide present. That is advantageous because the $^{18}$F-labelled cMBP is a radiotracer, present at and administered in extremely low chemical concentration—hence, if not removed, the unlabelled cMBP would otherwise be present in large chemical excess. That has been established to be important for PET in vivo imaging applications, since otherwise the unlabelled cMBP competes effectively with the $^{18}$F-labelled cMBP for the c-Met binding sites in vivo. It thus has a deleterious effect on the uptake and hence signal-to-background ratio in vivo. This issue was not reported in the prior art, since eg. when c-Met binding peptides are labelled with optical reporter dyes, the chemical amounts of labelled peptide involved are substantially greater than for PET, and hence the competition issue does not arise.

The imaging agent compositions of the present invention also overcome a previously unrecognised problem wherein, radiolabelled cMBP peptides suffer adhesion problems to various materials, including filters. Solubilised compositions are provided, which means that $^{18}$F-labelled cMBP radiotracers can be prepared and subjected to sterile filtration without significant loss of radiotracer due to adsorption to the filter.

BRIEF DESCRIPTION OF THE DRAWINGS

FIG. 1 illustrates the FASTLAB™ chemistry synthesizer platform configuration for Example 11.

DETAILED DESCRIPTION OF THE INVENTION

In a first aspect, the present invention provides an imaging agent which comprises an $^{18}$F-radiolabelled c-Met binding cyclic peptide, wherein said c-Met binding cyclic peptide is an 18 to 30-mer cyclic peptide of Formula I:

$$Z^1\text{-[cMBP]-}Z^2 \quad (I)$$

where:
cMBP is of Formula II:

$$\text{-(A)}_x\text{-Q-(A')}_y\text{-} \quad (II)$$

where Q is the amino acid sequence (SEQ ID NO: 1):

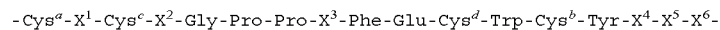

wherein $X^1$ is Asn, H is or Tyr;
  $X^2$ is Gly, Ser, Thr or Asn;
  $X^3$ is Thr or Arg;
  $X^4$ is Ala, Asp, Glu, Gly or Ser;
  $X^5$ is Ser or Thr;
  $X^6$ is Asp or Glu;
  and $Cys^{a-d}$ are each cysteine residues such that residues a and b as well as c and d are cyclised to form two separate disulfide bonds;
  A and A' are independently any amino acid other than Cys, with the proviso that at least one of A and A' is present and is Lys;
  x and y are independently integers of value 0 to 13, and are chosen such that [x+y]=1 to 13;
  $Z^1$ is attached to the N-terminus of cMBP, and is H or $M^{IG}$;
  $Z^2$ is attached to the C-terminus of cMBP and is OH, $OB^c$, or $M^{IG}$,
  where $B^c$ is a biocompatible cation;
  each $M^{IG}$ is independently a metabolism inhibiting group which is a biocompatible group which inhibits or suppresses in vivo metabolism of the cMBP peptide;
  wherein cMBP is labelled at the Lys residue of the A or A' groups with $^{18}$F.

By the term "imaging agent" is meant a compound suitable for imaging the mammalian body. Preferably, the mammal is an intact mammalian body in vivo, and is more preferably a human subject. Preferably, the imaging agent can be administered to the mammalian body in a minimally invasive manner, i.e. without a substantial health risk to the mammalian subject when carried out under professional medical expertise. Such minimally invasive administration is preferably intravenous administration into a peripheral vein of said subject, without the need for local or general anaesthetic.

The term "in vivo imaging" as used herein refers to those techniques that non-invasively produce images of all or part of an internal aspect of a mammalian subject.

By the term "c-Met binding cyclic peptide" is meant a peptide which binds to the hepatocyte growth factor receptor, also known as c-Met (or simply MET). Suitable such peptides of the present invention are cyclic peptides of 18 to 30 amino acids of Formula I. Such peptides have an apparent $K_D$ for c-Met of less than about 20 nM. The cMBP sequence of said peptides comprises proline residues, and it is known that such residues can exhibit cis/trans isomerisation of the backbone amide bond. The cMBP peptides of the present invention include any such isomers.

The $Z^1$ group substitutes the amine group of the last amino acid residue of the cMBP, i.e., the amino terminus. Thus, when $Z^1$ is H, the amino terminus of the cMBP terminates in a free $NH_2$ group of the last amino acid residue. The $Z^2$ group substitutes the carbonyl group of the last amino acid residue of the cMBP—i.e. the carboxy terminus. Thus, when $Z^2$ is OH, the carboxy terminus of the cMBP terminates in the free $CO_2H$ group of the last amino acid residue, and when $Z^2$ is $OB^c$ that terminal carboxy group is ionised as a $CO_2B^c$ group.

By the term "biocompatible cation" ($B^c$) is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium.

By the term "metabolism inhibiting group" ($M^{IG}$) is meant a biocompatible group which inhibits or suppresses in vivo metabolism of the cMBP peptide at either the amino terminus ($Z^1$) or carboxy terminus ($Z^2$). Such groups are well known to those skilled in the art and are suitably chosen from, for the peptide amine terminus: N-acylated groups —NH(C=O)$R^G$ where the acyl group —(C=O)$R^G$ has $R^G$ chosen from: $C_{1-6}$ alkyl, or $C_{3-10}$ aryl groups or comprises a polyethyleneglycol (PEG) building block. For the peptide carboxy terminus: carboxamide, tert-butyl ester, benzyl ester, cyclohexyl ester, amino alcohol or a polyethyleneglycol (PEG) building block. Preferred such PEG groups are the biomodifiers of Formula IA or IB:

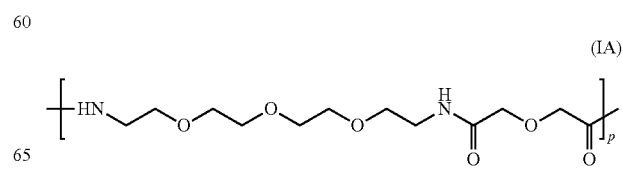

(IA)

17-amino-5-oxo-6-aza-3,9,12,15-tetraoxaheptadecanoic acid of Formula IA wherein p is an integer from 1 to 10. Alternatively, a PEG-like structure based on a propionic acid derivative of Formula IB can be used:

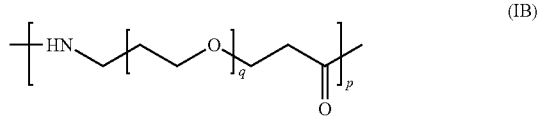

(IB)

where p is as defined for Formula IA and
q is an integer from 3 to 15.

In Formula IB, p is preferably 1 or 2, and q is preferably 5 to 12.

Preferred such amino terminus $M^{IG}$ groups are acetyl, benzyloxycarbonyl or trifluoroacetyl, most preferably acetyl.

By the term "$^{18}$F-radiolabelled" is meant that the c-Met binding cyclic peptide has covalently conjugated thereto the radioisotope $^{18}$F. The $^{18}$F is suitably attached via a C—F fluoroalkyl or fluoroaryl bond, since such bonds are relatively stable in vivo, and hence confer resistance to metabolic cleavage of the $^{18}$F radiolabel from the cMBP peptide. The $^{18}$F is preferably attached via a C—F fluoroaryl bond. The $^{18}$F may be attached directly to one of the amino acids of the cMBP, but is preferably conjugated as part of a radiofluorinated substituent on the cMBP. Said substituents are preferably of formula:

-(L)$_n$-$^{18}$F where:
L is a synthetic linker group of formula -(A1)$_m$- wherein each A1 is independently —CR$_2$—, —CR═CR—, —C≡C—, —CR$_2$CO$_2$—, —CO$_2$CR$_2$—, —NR(C═O)—, —(C═O)NR—, —NR(C═O)NR—, —NR(C═S)NR—, —SO$_2$NR—, —NRSO$_2$—CR$_2$OCR$_2$—, —CR$_2$SCR$_2$—, —CR$_2$NRCR$_2$—, —CR$_2$—O—N═, —CR$_2$—O—NR—, —CR$_2$—O—NH(CO)—, a C$_{4-8}$ cycloheteroalkylene group, a C$_{4-8}$ cycloalkylene group, a C$_{5-12}$ arylene group, or a C$_{3-12}$ heteroarylene group, an amino acid, a sugar or a monodisperse polyethyleneglycol (PEG) building block;
each R is independently chosen from H, C$_{1-4}$ alkyl, C$_{2-4}$ alkenyl, C$_{2-4}$ alkynyl, C$_{1-4}$ alkoxyalkyl or C$_{1-4}$ hydroxyalkyl;
m is an integer of value 1 to 20;
n is an integer of value 0 or 1.

By the term "amino acid" is meant an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)].

By the term "peptide" is meant a compound comprising two or more amino acids, as defined above, linked by a peptide bond (i.e. an amide bond linking the amine of one amino acid to the carboxyl of another).

By the term "sugar" is meant a mono-, di- or tri-saccharide. Suitable sugars include: glucose, galactose, maltose, mannose, and lactose. Optionally, the sugar may be functionalised to permit facile coupling to amino acids. Thus, eg. a glucosamine derivative of an amino acid can be conjugated to other amino acids via peptide bonds. The glucosamine derivative of asparagine (commercially available from NovaBiochem) is one example of this:

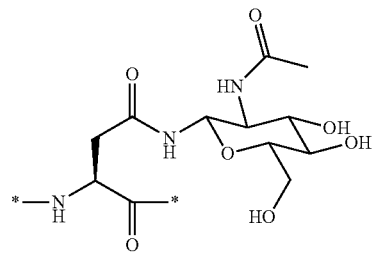 [SMILES: *N[C@@H](CC(=O)NC1OC(CO)C(O)C(O)C1NC(C)=O)C(*)=O]

When A and A' are "any amino acid other than Cys" that means that the additional amino acid of the A and A' groups lack free thiol groups, in particular Cys residues. That is because an additional Cys residue would risk disulfide bridge scrambing with the Cys$^a$-Cys$^b$ and Cys$^c$-Cys$^d$ disulfide bridges of the Q sequence, with consequent loss or reduction of c-Met binding affinity.

Preferred Features.

Preferred cMBP peptides of the present invention have a $K_D$ for binding of c-Met to c-Met/HGF complex of less than about 10 nM (based on fluorescence polarisation assay measurements), most preferably in the range 1 to 5 nM, with less than 3 nM being the ideal.

The cMBP peptide of Formulae I and II is preferably of Formula IIA:

-(A)$_x$-Q-(A')$_z$-Lys-     (IIA)

wherein A is as defined for Formula II,
z is an integer of value 0 to 12, and [x+z]=0 to 12,
and cMBP comprises only one Lys residue.

Thus, in Formula IIA the single Lys residue is located specifically at the C-terminus of the cMBP. That in turn means that the $^{18}$F radiolabel is preferably located at the C-terminus position.

Q preferably comprises the amino acid sequence of either SEQ ID NO: 2 or SEQ ID NO: 3:

(SEQ-2)

Ser-Cys$^a$-X$^1$-Cys$^c$-X$^2$-Gly-Pro-Pro-X$^3$-Phe-Glu-Cys$^d$-Trp-Cys$^b$-Tyr-X$^4$-X$^5$-X$^6$;

(SEQ-3)

Ala-Gly-Ser-Cys$^a$-X$^1$-Cys$^c$-X$^2$-Gly-Pro-Pro-X$^3$-Phe-Glu-Cys$^d$-Trp-Cys$^b$-Tyr-

X$^4$-X$^5$-X$^6$-Gly-Thr.

In SEQ ID NO: 1, SEQ ID NO: 2 and SEQ ID NO: 3, $X^3$ is preferably Arg. In Formula I and Formula II, the $-(A)_x$- or $-(A')_y$-groups preferably comprise a linker peptide which is chosen from:

```
                                           (SEQ ID NO: 4)
    -Gly-Gly-Gly-Lys-, (SEQ ID NO: 5)
    -Gly-Ser-Gly-Lys-
    or (SEQ ID NO: 6)
    -Gly-Ser-Gly-Ser-Lys-.
```

The cMBP peptide of the first aspect preferably has the amino acid sequence (SEQ ID NO: 7):

Ala-Gly-Ser-Cys$^a$-Tyr-Cys$^c$-Ser-Gly-Pro-Pro-Arg-Phe-Glu-Cys$^d$-Trp-Cys$^b$-Tyr-Glu-Thr-Glu-Gly-Thr-Gly-Gly-Lys.

Preferred imaging agents of the present invention have both cMBP peptide termini protected by $M^{IG}$ groups, i.e. preferably both $Z^1$ and $Z^2$ are $M^{IG}$, which will usually be different. Having both peptide termini protected in this way is important for in vivo imaging applications, since otherwise rapid peptide metabolism would be expected with consequent loss of selective binding affinity for c-Met. When both $Z^1$ and $Z^2$ are $M^{IG}$, preferably $Z^1$ is acetyl and $Z^2$ is a primary amide. Most preferably, $Z^1$ is acetyl and $Z^2$ is a primary amide and the $^{18}F$ moiety is attached to the epsilon amine side chain of a lysine residue of cMBP.

The radiofluorinated substituent $-(L)_n-^{18}F$ may be attached to the alpha amino group of the N-terminus of the c-Met binding peptide, or alternatively to the amine side chain of any amino-substituted amino acids (e.g. Lys residues). Preferably, it is attached to the epsilon ($\epsilon$) amine group of the Lys residue of the cMBP.

Preferred radiofluorinated substituents $-(L)_n-^{18}F$ have n=1, i.e. a synthetic linker group as defined above is present. More preferred such substituents comprise the $^{18}F$ radiolabel bound to a phenyl group, i.e. the substituent is of formula:

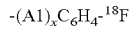

where: A1 is as defined above,
x is an integer of value 0 to 5.

Most preferred such substituents arise from either N-acylation of the Lys amine residue with a fluorinated active ester, or condensation of an amino-oxy derivative of the Lys amine residue with a fluorinated benzaldehyde, and are of formula:

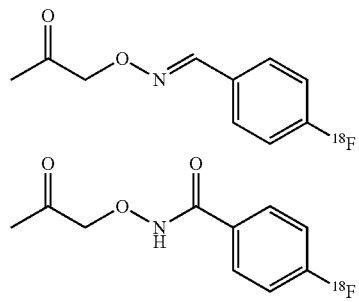

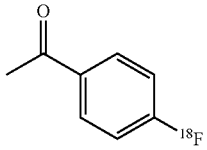

The imaging agents of the first aspect can be prepared as described in the fifth aspect (below).

In a second aspect, the present invention provides an imaging agent composition which comprises:
(i) the $^{18}F$-radiolabelled c-Met binding cyclic peptide of the first aspect;
(ii) an unlabelled c-Met binding cyclic peptide;

wherein: said c-Met binding cyclic peptide has the same amino acid sequence in (i) and (ii)
and wherein the unlabelled cMBP peptide is present in said composition at no
more than 50 times the molar amount of said $^{18}F$-labelled cMBP peptide.

Preferred embodiments of the $^{18}F$-radiolabelled c-Met binding cyclic peptide in the second aspect are as described in the first aspect (above).

The term "composition" has its conventional meaning, i.e. a mixture of the specified components. The composition may be in solid or liquid/solution form.

By the term "unlabelled" is meant that the c-Met binding cyclic peptide is non-radioactive, i.e. is not radiolabelled with $^{18}F$, or any other radioisotope. One or more such peptides may be present in the composition, and such unlabelled peptides primarily include the non-radioactive precursors of the fourth aspect (below). The term 'unlabelled' excludes the c-Met binding cyclic peptide labelled with $^{19}F$, where said $^{19}F$ is present in the $^{18}F$-fluoride used to radiolabel said c-Met binding cyclic peptide and is thus a product of the same radiolabelling reaction. As is known in the art, if two fluorine-substituted compounds differ only in the isotopes of the fluorine atom, they would behave chemically in an almost identical manner, and hence their separation would be extremely difficult. The unlabelled c-Met binding cyclic peptide or precursor preferably has the groups $Z^1$ and/or $Z^2$ already attached. The present inventors have found that, when an $^{18}F$-labelled aldehyde is used to conjugate to an aminooxy-functionalised cMBP peptide precursor, that non-radioactive aldehydic impurities are the principal sources of side-products. An important such aldehydic impurity in $^{18}F$-benzaldehyde is DMAP (i.e. 4-dimethylamino)benzaldehyde. Hence, the conjugation products of non-radioactive aldehydes (such as DMAP) with aminooxy-functionalised cMBP peptide are also within the scope of the term 'unlabelled c-Met binding cyclic peptide'.

Preferably, the unlabelled c-Met binding cyclic peptide is present in said composition at up to 30, more preferably up to 20, most preferably less than 10 times the molar amount of the corresponding $^{18}F$-labelled peptide.

The composition of the second aspect is preferably in solution form, wherein the components (i) and (ii) are both present in solution. More preferably, the solution is a biocompatible solvent, or mixture of two or more such solvents.

Preferred such biocompatible solvents are described in the third aspect (below), and preferably comprises an aqueous solvent.

The present inventors have found that, at radiotracer concentrations—an approximate concentration range of 1 to 50 μg/ml, the $^{18}$F-labelled cMBP peptides of the invention exhibit unwanted binding to a variety of materials. Since the radiotracer is present at such very low concentration, even a small chemical amount of adsorption can represent a significant percentage of the radioisotope present. That radiotracer concentration is to be compared with e.g. the corresponding cyanine dye-labelled c-Met binding peptides, where the concentration would be approximately 2 to 10 mg/ml—a factor of almost a thousand higher. In such cases, loss of μg amounts of material to adsorption would be an insignificant percentage of the dye-labelled peptides still in solution. The materials where radiotracer adhesion have been observed include plastics, glass and silica. In the case of filters, that can mean high percentage losses of radioactivity when carrying out sterile filtration.

The present inventors have found that the above adhesion phenomenon stems from the fact that the cMBP peptide precipitates under acidic conditions (particularly at lower temperatures). It is therefore preferred to maintain the composition at or above pH 7.5, more preferably pH 8.0 or above in order to keep the desired $^{18}$F-labelled c-Met binding peptide in solution, and thus avoiding loss of material. As an alternative to, or in addition to the use of controlled pH, a solubiliser may be included.

By the term "solubiliser" is meant an additive present in the composition which increases the solubility of the imaging agent in the solvent. A preferred such solvent is aqueous media, and hence the solubiliser preferably improves solubility in water. Suitable such solubilisers include: $C_{1-4}$ alcohols; glycerine; polyethylene glycol (PEG); propylene glycol; polyoxyethylene sorbitan monooleate; sorbitan monooloeate; polysorbates; poly(oxyethylene)poly(oxypropylene)poly(oxyethylene) block copolymers (PLURONICS™ brand poloxamers); cyclodextrins (e.g. alpha, beta or gamma cyclodextrin, hydroxypropyl-β-cyclodextrin or hydroxypropyl-γ-cyclodextrin) and lecithin.

Preferred solubilisers are cyclodextrins, $C_{1-4}$ alcohols and PLURONICS™ brand poloxamers, more preferably cyclodextrins and $C_{2-4}$ alcohols. When the solubiliser is an alcohol, it is preferably ethanol or propanol, more preferably ethanol. Ethanol has a potential dual role, since it can also function as a radioprotectant. When the solubiliser is a cyclodextrin, it is preferably a cyclodextrin, more preferably hydroxypropyl-β-cyclodextrin (HPCD). The concentration of cyclodextrin can be from about 0.1 to about 40 mg/mL, preferably between about 5 and about 35 mg/mL, more preferably 20 to 30 mg/ml, most preferably around 25 mg/ml. When a single solubiliser is used, it is preferably ethanol or hydroxypropyl-β-cyclodextrin, more preferably ethanol. When a combination of solubilisers is used, it is preferably ethanol and to hydroxypropyl-β-cyclodextrin.

Preferably, the composition of the second aspect is maintained at pH at or above 7.5, optionally with 5-10% v/v ethanol as solubiliser.

The imaging agent composition of the second aspect preferably further comprises one or more radioprotectants. By the term "radioprotectant" is meant a compound which inhibits degradation reactions, such as redox processes, by trapping highly-reactive free radicals, such as oxygen-containing free radicals arising from the radiolysis of water. A combination of two or more different radioprotectants may be used. The radioprotectants of the present invention are suitably chosen from: ethanol; ascorbic acid; para-aminobenzoic acid (i.e. 4-aminobenzoic acid or pABA); gentisic acid (i.e. 2,5-dihydroxybenzoic acid), and where applicable salts of such acids with a biocompatible cation as define above. The radioprotectant of the present invention preferably comprises para-aminobenzoic acid or sodium para-aminobenzoate.

A most preferred imaging agent composition of the present invention comprises the cMBP peptide of SEQ-7 having $Z^1=Z^2=M^{IG}$ attached, and a combination of para-aminobenzoic acid radioprotectant and ethanol radioprotectant/solubiliser in aqueous buffer. A preferred peptide of SEQ-7 in such preferred compositions is Peptide 1, and a preferred $^{18}$F-labelled cMBP peptide is Compound 3. The radioactive concentration is preferably less than 350 MBq/ml, with a pABA concentration of 2 mg/ml, and ethanol at about 5-10% vol/vol, preferably 6.5-7.5% vol/vol.

In a third aspect, the present invention provides a pharmaceutical composition which comprises the imaging agent of the first aspect, or the imaging agent composition of the second aspect, together with a biocompatible carrier, in a sterile form suitable for mammalian administration.

Preferred aspects of the imaging agent and composition in the third aspect are as defined in the first and second aspects respectively.

The "biocompatible carrier" is a fluid, especially a liquid, in which the imaging agent can be suspended or preferably dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). Preferably the biocompatible carrier is pyrogen-free water for injection, isotonic saline or phosphate buffer. Use of a buffer is preferred in order to control pH.

The imaging agents and biocompatible carrier are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour.

Preferred multiple dose containers comprise a single bulk vial (e.g. of 10 to 30 cm$^3$ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and are therefore preferably a disposable or other syringe suitable for clinical use. The pharmaceutical compositions of the present invention preferably have a dosage suitable for a single patient and are provided in a suitable syringe or container, as described above.

The pharmaceutical composition may contain additional optional excipients such as: an antimicrobial preservative, pH-adjusting agent, filler, radioprotectant, solubiliser or osmolality adjusting agent. The terms "radioprotectant" and "solubiliser" and preferred embodiments thereof are as described in the second aspect (above). By the term "antimicrobial preservative" is meant an agent which inhibits the growth of potentially harmful micro-organisms such as bacteria, yeasts or moulds. The antimicrobial preservative may also exhibit some bactericidal properties, depending on the dosage employed. The main role of the antimicrobial preservative(s) of the present invention is to inhibit the growth of any such micro-organism in the pharmaceutical composition. The antimicrobial preservative may, however, also optionally be used to inhibit the growth of potentially harmful micro-organisms in one or more components of kits used to prepare said composition prior to administration. Suitable antimicrobial preservative(s) include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the composition is within acceptable limits (approximately pH 4.0 to 10.5) for human or mammalian administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. When the composition is employed in kit form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

The pharmaceutical compositions of the third aspect may be prepared under aseptic manufacture (i.e. clean room) conditions to give the desired sterile, non-pyrogenic product. It is preferred that the key components, especially the associated reagents plus those parts of the apparatus which come into contact with the imaging agent (eg. vials) are sterile. The components and reagents can be sterilised by methods known in the art, including: sterile filtration, terminal sterilisation using e.g. gamma-irradiation, autoclaving, dry heat or chemical treatment (e.g. with ethylene oxide). It is preferred to sterilise some components in advance, so that the minimum number of manipulations needs to be carried out. As a precaution, however, it is preferred to include at least a sterile filtration step as the final step in the preparation of the pharmaceutical composition.

As noted above, the pharmaceutical compositions of the present invention are preferably maintained at pH 7.5 or above and/or comprise a solubiliser, so that a sterile filtration step may be used without undue loss of radioactivity adsorbed to the filter material. Similar considerations apply to manipulations of the pharmaceutical compositions in clinical grade syringes, or using plastic tubing, where adsorption may cause loss of radioactivity without the use of a solubiliser.

The pharmaceutical composition is preferably prepared as described in the sixth aspect (below).

The pharmaceutical composition of the third aspect may optionally be prepared from a kit. Such kits comprise the c-Met binding peptide of Formula I as described in the first aspect or the precursor of the fourth aspect in sterile, apyrogenic form such that, upon reaction with a sterile supply of the radioisotope $^{18}F$ in a suitable solvent, radiolabelling occurs to give the desired $^{18}F$-labelled c-Met binding peptide.

For the kit, the c-Met binding peptide or precursor, plus other optional excipients as described above, are preferably provided as a lyophilised powder in a suitable vial or container. The agent is then designed to be reconstituted either with $^{18}F$ in a biocompatible carrier directly (i.e. as a reconstitution), or first reconstitution of the kit with a biocompatible carrier, followed by reaction with a supply of $^{18}F$.

A preferred sterile form of the c-Met binding peptide or precursor is a lyophilised solid. The sterile, solid form is preferably supplied in a pharmaceutical grade container, as described for the pharmaceutical composition (above). When the kit is lyophilised, the formulation may optionally comprise a cryoprotectant chosen from a saccharide, preferably mannitol, maltose or tricine.

In a fourth aspect, the present invention provides a precursor, useful in the preparation of the $^{18}F$-radiolabelled c-Met binding cyclic peptide of the third aspect, or the composition of the first or second aspects, which comprises:
  (i) the c-Met binding cyclic peptide of Formula I as defined in the first aspect, wherein $Z^1=Z^2=M^{IG}$; or
  (ii) an amino-oxy functionalised c-Met binding cyclic peptide.

By the term "amino-oxy functionalised c-Met binding cyclic peptide" is meant the c-Met binding cyclic peptide of Formula I having covalently conjugated thereto an amino-oxy functional group. Such amino-oxy groups are of formula —O—NH$_2$, preferably —CH$_2$O—NH$_2$ and have the advantage that the amine of the amino-oxy group is more reactive than a Lys amine group in condensation reactions with aldehydes to form oxime ethers. Such amino-oxy groups are suitably attached at the Lys residue of the cMBP, as described below.

The precursor is non-radioactive, and is designed so that it can be obtained in a high degree of chemical purity. It is also designed so that, upon reaction with a suitable source of $^{18}F$, reaction occurs efficiently with satisfactory radiochemical purity (RCP). The "suitable source of $^{18}F$" depends on the nature of the precursor. When the precursor comprises the unlabelled c-Met binding peptide of Formula I, the amine group of the lysine (Lys) residue of the unlabelled peptide is designed to be the site of radiolabelling. The termini of the cMBP peptide are protected, since $Z^1=Z^2=M^{IG}$. Preferred such c-Met binding peptides and preferred $Z^1/Z^2$ groups are as described in the first aspect. Thus, the suitable source of $^{18}F$ is designed to react as efficiently as possible with the lysine amine group, preferably the Lys epsilon amine.

For the preparation of the pharmaceutical composition of the third aspect, the precursor is preferably in sterile form, more preferably a lyophilised solid.

The precursor of the fourth aspect is preferably an amino-oxy functionalised c-Met binding peptide.

c-Met binding peptides of Formula I, i.e. $Z^1$-[cMBP]-$Z^2$ of the present invention may be obtained by a method of preparation which comprises:
(i) solid phase peptide synthesis of a linear peptide which has the same peptide sequence as the desired cMBP peptide and in which the $Cys^a$ and $Cys^b$ are unprotected, and the $Cys^c$ and $Cys^d$ residues have thiol-protecting groups;
(ii) treatment of the peptide from step (i) with aqueous base in solution to give a monocyclic peptide with a first disulphide bond linking $Cys^a$ and $Cys^b$;
(iii) removal of the $Cys^c$ and $Cys^d$ thiol-protecting groups and cyclisation to give a second disulphide bond linking $Cys^c$ and $Cys^d$, which is the desired bicyclic peptide product $Z^1$-[cMBP]-$Z^2$.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Amine protecting groups are well known to those skilled in the art and are suitably chosen from: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl). Suitable thiol protecting groups are Trt (Trityl), Acm (acetamidomethyl), t-Bu (tert-butyl), tert-Butylthio, methoxybenzyl, methylbenzyl or Npys (3-nitro-2-pyridine sulfenyl). The use of further protecting groups are described in 'Protective Groups in Organic Synthesis', $4^{th}$ Edition, Theorodora W. Greene and Peter G. M. Wuts, [Wiley Blackwell, (2006)]. Preferred amine protecting groups are Boc and Fmoc, most preferably Boc. Preferred amine protecting groups are Trt and Acm.

Examples 1 and 2 provide further specific details. Further details of solid phase peptide synthesis are described in P. Lloyd-Williams, F. Albericio and E. Girald; *Chemical Approaches to the Synthesis of Peptides and Proteins*, CRC Press, 1997. The cMBP peptides are best stored under inert atmosphere and kept in a freezer. When used in solution, it is best to avoid pH above 7 since that risks scrambling of the disulfide bridges.

Amino-oxy functionalised c-Met binding peptides can be prepared by the methods of Poethko et al [J. Nucl. Med., 45, 892-902 (2004)], Schirrmacher et al [Bioconj. Chem., 18, 2085-2089 (2007)], Solbakken et al [Bioorg. Med. Chem. Lett, 16, 6190-6193 (2006)] or Glaser et al [Bioconj. Chem., 19, 951-957 (2008)]. The amino-oxy group may optionally be conjugated in two steps. First, the N-protected amino-oxy carboxylic acid or N-protected amino-oxy activated ester is conjugated to the c-Met binding peptide. Second, the intermediate N-protected amino-oxy functionalised c-Met binding peptide is deprotected to give the desired product [see Solbakken and Glaser papers cited above]. N-protected amino-oxy carboxylic acids such as Boc-NH—O—$CH_2$ (C=O)OH are commercially available, e.g. from Novabiochem.

In a fifth aspect, the present invention provides a method of preparation of the $^{18}$F-radiolabelled c-Met binding cyclic peptide of the first aspect, which comprises:
(i) provision of the precursor of the fourth aspect;
(ii) when said precursor comprises an unlabelled c-Met binding cyclic peptide of Formula I wherein $Z^1$=$Z^2$ reaction with either an $^{18}$F-labelled activated ester, or an $^{18}$F-labelled carboxylic acid in the presence of an activating agent, to give the $^{18}$F-radiolabelled c-Met binding cyclic peptide conjugated via an amide linkage at the Lys residue of the cMBP of said cyclic peptide;
(iii) when said precursor comprises an amino-oxy functionalised c-Met binding cyclic peptide, reaction with either:
(a) an $^{18}$F-labelled activated ester, or an $^{18}$F-labelled carboxylic acid in the presence of an activating agent, to give the $^{18}$F-radiolabelled c-Met binding cyclic peptide conjugated via an amide linkage at the amino-oxy position of said functionalised peptide; or
(b) an $^{18}$F-labelled aldehyde to give the $^{18}$F-radiolabelled c-Met binding cyclic peptide conjugated via an oxime ether linkage at the amino-oxy position of said functionalised peptide.

By the term "activated ester" or "active ester" is meant an ester derivative of the associated carboxylic acid which is designed to be a better leaving group, and hence permit more facile reaction with nucleophile, such as amines. Examples of suitable active esters are: N-hydroxysuccinimide (NETS); sulfo-succinimidyl ester; pentafluorophenol; pentafluorothiophenol; para-nitrophenol; hydroxybenzotriazole and PyBOP (i.e. benzotriazol-1-yl-oxytripyrrolidinophosphonium hexafluorophosphate). Preferred active esters are N-hydroxysuccinimide or pentafluorophenol esters, especially N-hydroxysuccinimide esters.

By the term "activating agent" is meant a reagent used to facilitate coupling between an amine and a carboxylic acid to generate an amide. Suitable such activating agents are known in the art and include carbodiimides such as EDC [N-(3-dimethylaminopropyl)-N'-ethylcarbodiimide and N,N'-dialkylcarbodiimides such as dicyclohexylcarbodiimide or diisopropylcarbodiimide; and triazoles such as HBTU [O-(benzotriazol-1-yl)-N,N,N',N'-tetramethyluronium hexafluorophosphate], HATU [O-(7-azabenzotriazol-1-yl)-N,N,N',N'-tetramethyluronium hexafluorophosphate], and PyBOP [benzotriazol-1-yloxy)tripyrrolidinophosphonium hexafluorophosphate]. Further details are given in *"March's Advanced Organic Chemistry"*, $5^{th}$ Edition, pages 508-510, Wiley Interscience (2001). A preferred such activating agent is EDC.

$^{18}$F-labelled activated esters, such as [$^{18}$F]SFB can be prepared by the method of Glaser et al, and references therein [J. Lab. Comp. Radiopharm., 52, 327-330 (2009)], or the automated method of Marik et al [Appl. Rad. Isot., 65(2), 199-203 (2007)]:

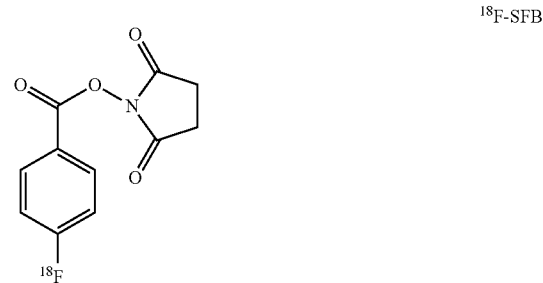 [SMILES: O=C(ON1C(=O)CCC1=O)c1ccc([18F])cc1]

$^{18}$F-SFB $^{18}$F-labelled carboxylic acids can be obtained by the method of Marik et al cited above. $^{18}$F-labelled aliphatic aldehydes of formula $^{18}F(CH_2)_2O[CH_2CH_2O]_qCH_2CHO$, where q is 3, can be obtained by the method of Glaser et al [Bioconj. Chem., 19(4), 951-957 (2008)]. $^{18}$F-fluorobenzaldehyde can be obtained by the method of Glaser et al [J. Lab. Comp. Radiopharm., 52, 327-330 (2009)]. The precursor Me$_3$N$^+$—C$_6$H$_4$—CHO. CF$_3$SO$_3^-$ is obtained by the method of Haka et al [J. Lab. Comp. Radiopharm., 27, 823-833 (1989)].

The conjugation of $^{18}$F-labelled aldehydes to amino-oxy functionalised c-Met peptides is preferably carried out in the presence of an aniline catalyst as described by Flavell et al [J. Am. Chem. Soc., 130(28), 9106-9112 (2008)]. Whilst it is possible to use protected amino-oxy c-Met peptides (such as Compound 1) as precursors, the free amino-oxy derivative (such as Compound 2) is preferred. That is because the whole synthesis is more amenable to automation, whereas with the protected precursor, a manual deprotection step is typically required.

In a sixth aspect, the present invention provides a method of preparation of the imaging agent composition of the second aspect, or the pharmaceutical composition thereof of the third aspect, which comprises:
  (i) preparing the $^{18}$F-radiolabelled c-Met binding cyclic peptide as defined in the method of preparation of the fifth aspect;
  (ii) chromatographic separation of the unlabelled c-Met binding cyclic peptide from the $^{18}$F-radiolabelled c-Met binding cyclic peptide.

Preferred aspects of the imaging agent composition and pharmaceutical composition in the sixth aspect are as described in the second and third aspect respectively.

The chromatographic separation of step (ii) may be carried out by HPLC or SPE (solid phase extraction) using one or more SPE cartridge(s). SPE is preferred when an automated synthesizer is used, and HPLC is preferred in other circumstances. Example 5 provides a suitable HPLC method for Compound 3 of the present invention.

The method of the sixth aspect is preferably used to obtain the pharmaceutical composition of the third aspect. When the method is used to provide the pharmaceutical composition of the third aspect, the method of preparation is preferably carried out using an automated synthesizer apparatus.

By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical composition is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer preferably comprises a cassette. By the term "cassette" is meant a piece of apparatus designed to fit removably and interchangeably onto an automated synthesizer apparatus (as defined below), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (eg. SPE). The cassette always comprises a reaction vessel. Such reaction vessels are preferably 1 to 10 cm$^3$, most preferably 2 to 5 cm$^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture and are therefore manufactured from materials which are of pharmaceutical grade and ideally also are resistant to radiolysis.

Preferred automated synthesizers of the present invention are those which comprise a disposable or single use cassette which comprises all the reagents, reaction vessels and apparatus necessary to carry out the preparation of a given batch of radiofluorinated radiopharmaceutical. The cassette means that the automated synthesizer has the flexibility to be capable of making a variety of different radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

Included in this aspect of the invention, is the use of an automated synthesizer apparatus to prepare the pharmaceutical composition of the second aspect.

In a seventh aspect, the present invention provides a method of imaging of the mammalian body in vivo to obtain images of sites of c-Met over-expression or localisation, which method comprises imaging said body to which the imaging agent of the first aspect, the imaging agent composition of the second aspect or the pharmaceutical composition of the third aspect, had been previously administered.

Preferred aspects of the imagine agent, imaging agent composition and pharmaceutical composition in the seventh aspect are as described in the first, second and third aspects respectively.

Preferably, the mammal is an intact mammalian body in vivo, and is more preferably a human subject. Preferably, the imaging agent can be administered to the mammalian body in a minimally invasive manner, i.e. without a substantial health risk to the mammalian subject even when carried out under professional medical expertise. Such minimally invasive administration is preferably intravenous administration into a peripheral vein of said subject, without the need for local or general anaesthetic.

Preferably, the pharmaceutical composition of the third aspect is used. In the method of imaging of the seventh aspect, the site of c-Met over-expression or localisation is preferably a cancerous tumour or metastasis. It is envisaged that the agent would be useful for imaging c-Met expression in both precancerous and cancerous tumours or metastases, potentially enabling selection of therapy. In addition, repeated imaging with such an imaging agent also has the potential to quickly and effectively monitor an individual subject's response to established and novel therapeutic regimens, thereby allowing discontinuation of ineffective treatment. Furthermore, as overexpression of c-Met is a potential attribute of aggressive tumours, it is anticipated that the c-Met imaging agent has the potential to discriminate between aggressive and less aggressive cancers at an early stage in their development.

Included in this aspect is a method of diagnosis of sites of c-Met over-expression or localisation within the mammalian body in vivo, which comprises the imaging method of the seventh aspect.

The invention is illustrated by the non-limiting Examples detailed below. Example 1 provides the synthesis of a cMBP peptide of the invention having metabolism inhibiting groups ($Z^1=Z^2=M^{IG}$) at both termini (Peptide 1). Example 2 provides the synthesis of a protected precursor of the invention (Compound 1). Example 3 provides the synthesis of the non-radioactive, fluorinated (i.e. $^{19}F$) counterpart of the fluorine-labelled c-Met peptide (Compound 3A). Example 4 provides the synthesis of an $^{18}F$-radiofluorinated c-Met peptide of the invention (Compound 3B). Example 5 provides HPLC conditions for the separation of labelled and unlabelled c-Met binding peptides.

Example 6 provides the biodistribution of an $^{18}F$-labelled peptide of the invention (Compound 3B) in an animal tumour model. The results show binding to the human c-Met receptor expressed in the HT-29 tumours, and hence utility for tumour imaging. Example 7 demonstrates that the tumour uptake of Example 6 is specific, since the uptake can be inhibited by co-administration of non-radioactive $^{19}F$-labelled c-Met binding peptide (Compound 3A). Example 8 also demonstrates reduced liver uptake of about 40% in primates when $^{19}F$-labelled c-Met binding peptide is co-administered. Co-administration of a $^{19}F$-labelled scrambled version of the peptide, which has no affinity for the c-Met receptor, did not significantly reduce the liver uptake. The liver has a high level of c-Met expression, and the reduction in uptake following competition with $^{19}F$-labelled cMBP is therefore believed to represent evidence of specific c-Met binding in vivo.

Example 9 shows that the solubiliser cyclodextrin has no significant effect on the biodistribution of Compound 3B in vivo. Example 10 compares the fully automated synthesis of Compound 3B (starting from Compound 2), with the partially automated synthesis starting from Compound 1. The use of Compound 2 is preferred because it gives higher yields, and deprotection of Compound 1 has the disadvantages of:
  (i) difficulty of establishing the degree of deprotection prior to radiolabelling;
  (ii) the TFA used to deprotect the peptide is not compatible with the plastic of the automated synthesizer apparatus.

Example 11 provides the automated synthesis of Compound 3B, further including automated use of SPE cartridge purification. The results show that Compound 3B can be obtained in high purity and satisfactory radiochemical yield using this approach. Example 12 provides the freeze-drying of a precursor of the invention. Example 13 demonstrates the effect of pH on an imaging agent of the invention. Example 14 describes human imaging using an imaging agent of the invention.

ABBREVIATIONS

Conventional single letter or 3-letter amino acid abbreviations are used.

% id: percentage injected dose
Ac: Acetyl
Acm: Acetamidomethyl
ACN: Acetonitrile
Boc: tert-Butyloxycarbonyl
DCM: Dichloromethane
DIPEA: N,N-Diisopropylethyl amine
DMF: Dimethylformamide
DMSO: Dimethylsulfoxide
EDC: N-3-dimethylaminopropyl)-N'-ethylcarbodiimide.
Fmoc: 9-Fluorenylmethoxycarbonyl
HBTU: O-Benzotriazol-1-yl-N,N,N',N'-tetramethyluronium hexafluorophosphate
HPLC: High performance liquid chromatography
HSPyU O—(N-succinimidyl)-N,N,N',N'-tetramethyleneuronium hexafluorophosphate
NETS: N-hydroxy-succinimide
NMM: N-Methylmorpholine
NMP: 1-Methyl-2-pyrrolidinone
pABA: para-aminobenzoic acid.
Pbf: 2,2,4,6,7-Pentamethyldihydrobenzofuran-5-sulfonyl
PBS: Phosphate-buffered saline
p.i.: post-injection
PyBOP: benzotriazol-1-yl-oxytripyrrolidinophosphonium hexafluorophosphate
tBu: tert-butyl
TFA: Trifluoroacetic acid
TIS: Triisopropylsilane
Trt: Trityl.

COMPOUNDS OF THE INVENTION

| Name | Structure |
|---|---|
| Peptide 1 | Disulfide bridges at Cys4-16 and Cys6-14;<br>Ac-Ala-Gly-Ser-Cys-Tyr-Cys-Ser-Gly-Pro-Pro-Arg-Phe-Glu-Cys-Trp-Cys-Tyr-Glu-Thr-Glu-Gly-Thr-Gly-Gly-Gly-Lys-NH$_2$<br>or<br>Ac-AGSCYCSGPPRFECWCYETEGTGGGK-NH$_2$ |
| Compound 1 | [Peptide 1]-NH-C(=O)-CH$_2$-O-NH-Boc |
| Compound 2 | [Peptide 1]-NH-C(=O)-CH$_2$-O-NH$_2$ |
| Compound 3 | [Peptide 1]-NH-C(=O)-CH$_2$-O-N=CH-C$_6$H$_4$-$^n$F<br>n = 19 Compound 3A;<br>n = 18 Compound 3B; | where:
Compounds 1, 2 and 3 are functionalised at the epsilon amine group of the carboxy terminal Lys of Peptide 1; Boc = tert-Butyloxycarbonyl.

Example 1

Synthesis of Peptide 1

Step (a): Synthesis of Protected Precursor Linear Peptide.

The precursor linear peptide has the structure Ac-SEQ ID NO: 7-NH$_2$:

Ac-Ala-Gly-Ser-Cys-Tyr-Cys(Acm)-Ser-Gly-Pro-Pro-Arg-Phe-Glu-Cys(Acm)-Trp-Cys-Tyr-Glu-Thr-Glu-Gly-Thr-Gly-Gly-Gly-Lys-NH$_2$

The peptidyl resin H-Ala-Gly-Ser(tBu)-Cys(Trt)-Tyr(tBu)-Cys(Acm)-Ser(tBu)-Gly-Pro-Pro-Arg(Pbf)-Phe-Glu(OtBu)-Cys(Acm)-Trp(Boc)-Cys(Trt)-Tyr(tBu)-Gly-Glu(OtBu)-Thr($\psi^{Me,Me}$pro)-Glu(OtBu)-Gly-Thr(tBu)-Gly-Gly-Gly-Lys(Boc)-Polymer was assembled on an Applied Biosystems 433A peptide synthesizer using Fmoc chemistry starting with 0.1 mmol Rink Amide Novagel resin. An excess of 1 mmol pre-activated amino acids (using HBTU) was applied in the coupling steps. Glu-Thr pseudoproline (Novabiochem 05-20-1122) was incorporated in the sequence. The resin was transferred to a nitrogen bubbler apparatus and treated with a solution of acetic anhydride (1 mmol) and NMM (1 mmol) dissolved in DCM (5 mL) for 60 min. The anhydride solution was removed by filtration and the resin washed with DCM and dried under a stream of nitrogen.

The simultaneous removal of the side-chain protecting groups and cleavage of the peptide from the resin was carried out in TFA (10 mL) containing 2.5% TIS, 2.5% 4-thiocresol and 2.5% water for 2 hours and 30 min. The resin was removed by filtration, TFA removed in vacuo and diethyl ether added to the residue. The formed precipitate was washed with diethyl ether and air-dried affording 264 mg of crude peptide.

Purification by preparative HPLC (gradient: 20-30% B over 40 min where A=H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 30 min) of the crude peptide afforded 100 mg of pure Peptide 1 linear precursor. The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3µ C18 (2) 50×2 mm, detection: UV 214 nm, product retention time: 6.54 min). Further product characterisation was carried out using electrospray mass spectrometry (MH$_2^{2+}$ calculated: 1464.6, MH$_2^{2+}$ found: 1465.1).

Step (b): Formation of Monocyclic Cys4-16 Disulfide Bridge.

Cys4-16; Ac-Ala-Gly-Ser-Cys-Tyr-Cys(Acm)-Ser-Gly-Pro-Pro-Arg-Phe-Glu-Cys(Acm)-Trp-Cys-Tyr-Glu-Thr-Glu-Gly-Thr-Gly-Gly-Gly-Lys-NH$_2$Ac-SEQ ID NO: 7-NH$_2$.

The linear precursor from step (a) (100 mg) was dissolved in 5% DMSO/water (200 mL) and the solution adjusted to pH 6 using ammonia. The reaction mixture was stirred for 5 days. The solution was then adjusted to pH 2 using TFA and most of the solvent removed by evaporation in vacuo. The residue (40 mL) was injected in portions onto a preparative HPLC column for product purification.

Purification by preparative HPLC (gradient: 0% B for 10 min, then 0-40% B over 40 min where A=H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 44 min) of the residue afforded 72 mg of pure Compound 1 monocyclic precursor.

The pure product (as a mixture of isomers P1 to P3) was analysed by analytical HPLC (gradient: 10-40% B over 10 min where A=H$_2$O/0.1% TFA and B=ACN/0.1% TFA, flow rate: 0.3 mL/min, column: Phenomenex Luna 3µ C18 (2) 50×2 mm, detection: UV 214 nm, product retention time: 5.37 min (P1); 5.61 min (P2); 6.05 min (P3)). Further product characterisation was carried out using electrospray mass spectrometry (MH$_2^{2+}$ calculated: 1463.6, MH$_2^{2+}$ found: 1464.1 (P1); 1464.4 (P2); 1464.3 (P3)).

Step (c): Formation of Second Cys6-14 Disulfide Bridge (Peptide 1).

The monocyclic precursor from step (b) (72 mg) was dissolved in 75% AcOH/water (72 mL) under a blanket of nitrogen. 1 M HCl (7.2 mL) and 0.05 M I$_2$ in AcOH (4.8 mL) were added in that order and the mixture stirred for 45 min. 1 M ascorbic acid (1 mL) was added giving a colourless mixture. Most of the solvents were evaporated in vacuo and the residue (18 mL) diluted with water/0.1 TFA (4 mL) and the product purified using preparative HPLC.

Purification by preparative HPLC (gradient: 0% B for 10 min, then 20-30% B over 40 min where A=H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 43-53 min) of the residue afforded 52 mg of pure Peptide 1.

The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3µ C18 (2) 50×2 mm, detection: UV 214 nm, product retention time: 6.54 min). Further product characterisation was carried out using electrospray mass spectrometry (MH$_2^{2+}$ calculated: 1391.5, MH$_2^{2+}$ found: 1392.5).

Example 2

Synthesis of Compound 1

(Boc-aminooxy)acetic acid (Sigma-Aldrich; 138 mg, 0.72 mmol), EDC (138 mg, 0.72 mmol) and N-hydroxysuccinimide (83 mg, 0.72 mmol) were dissolved in DMF (1 ml). The solution was shaken for 25 min, and then added to a solution of Peptide 1 (1.0 g, 0.36 mmol) in DMF (5 ml). The reaction mixture was stirred for 2 min. Sym.-collidine (239 µL, 1.80 mmol) was then added, and the reaction mixture stirred for 3 hours. The reaction mixture was diluted with water (5 ml), and the product purified by preparative RP-HPLC.

HPLC conditions: Waters Prep 4000 system, Solvent A=H$_2$O/0.1% TFA and Solvent B=ACN/0.1% TFA; gradient 20-40% B over 60 min; flow rate=50 ml/min; column: Phenomenex Luna 10 µm C18 (2) 250×50 mm; detection: uv 214 nm.

Yield of purified Compound 1690 mg (65%). Found m/z: 1478.4, expected MH$_2^{2+}$: 1478.1.

Example 3

Synthesis of Compound 3A

Step (a): Preparation of N-(4-fluorobenzylidene)aminooxyacetic acid.

(Boc-aminooxy)acetic acid (96 mg, 0.50 mmol) and 4-fluorobenzaldehyde (53 µL, 0.50 mmol) were dissolved in formic acid (0.5 ml), and the reaction mixture stirred for 135 mins. The reaction mixture was then diluted with 20% ACN/water/0.1% TFA (7 ml), and the product purified by semi-preparative RP-HPLC.

HPLC conditions: Beckman System Gold; Solvent A=H$_2$O/0.1% TFA and Solvent B=ACN/0.1% TFA; gradient 25-35% B over 40 min; flow rate=10 ml/min; column: Phenomenex Luna 5 μm C18 (2) 250×21.2 mm; detection: uv 214 nm.

Yield 92 mg (93%).

Step (b): Preparation of Compound 3A

N-(4-Fluorobenzylidene)aminooxyacetic acid [from Step (a), 43 mg, 0.22 mmol] and PyBOP (112 mg, 0.22 mmol) were dissolved in DMF (2 ml). A solution of DIPEA (157 μL, 0.90 mmol) in DMF (10 ml) was added, and the mixture shaken for 1 min. The solution was then added to a solution of Peptide 1 (500 mg, 0.18 mmol) in DMF (10 ml), and the reaction mixture shaken for 30 min. The reaction mixture was then diluted with water (20 ml), and the product purified by preparative HPLC.

HPLC conditions as per Example 2, except: Solvent A=H$_2$O/0.1% ammonium acetate and Solvent B=ACN. Yield 291 mg (55%) of pure material. Found m/z: 988.6, expected MH$_3^{3+}$: 987.7.

Example 4

Synthesis of Compound 3B from Compound 1

Step (a): Deprotection of Compound 1 to Give Compound 2.

Compound 1 (7 mg, 2.37 μM) in a 5-ml reaction vial was treated with water (10 μL) and trifluoroacetic acid (190 μL), and then immersed within a sealed vial in a sonic bath for 10 minutes. The aqueous TFA was then removed in vacuo (approximately 30 mins), and the residue reconstituted in citrate buffer (pH 2.6, 1.7 mL) and loaded onto an automated synthesizer cassette (FASTLAB™ chemistry synthesizer platform, GE Healthcare Ltd) at position 14.

Step (b) Synthesis and Purification of $^{18}$F-Benzaldehyde.

[$^{18}$F]fluoride was produced using a GEMS PETtrace cyclotron with a silver target via the [$^{18}$O](p,n) [$^{18}$F] nuclear reaction. Total target volumes of 1.5-3.5 mL were used. The radiofluoride was trapped on a Waters QMA cartridge (preconditioned with carbonate), and the fluoride is eluted with a solution of Kryptofix$_{2.2.2.}$ (4 mg, 10.7 μM) and potassium carbonate (0.56 mg, 4.1 μM) in water (80 μL) and acetonitrile (320 μL). Nitrogen was used to drive the solution off the QMA cartridge to the reaction vessel. The [$^{18}$F]fluoride was dried for 9 minutes at 120° C. under a steady stream of nitrogen and vacuum. Trimethylammonium benzaldehyde triflate, [Haka et al, J. Lab. Comp. Radiopharm., 27, 823-833 (1989)] (3.3 mg, 10.5 μM), in dimethylsulfoxide (1.1 mL) was added to the dried [$^{18}$F]fluoride, and the mixture heated at 105° C. for 7 minutes to produce 4-[$^{18}$F]fluorobenzaldehyde. The labelling efficiency was 69±3% decay corrected.

The crude labelling mixture was then diluted with ammonium hydroxide solution and loaded onto an MCX+ SPE cartridge (pre-conditioned with water as part of the FASTLAB™ chemistry synthesizer platform sequence). The cartridge was washed with water, dried with nitrogen gas before elution of 4-[$^{18}$F]fluorobenzaldehyde back to the reaction vessel in ethanol (1 mL). Approximately 13% (decay corrected) of [$^{18}$F]fluorobenzaldehyde remained trapped on the cartridge.

Step (c): Aldehyde Condensation with Amino-Oxy Derivative (Compound 2).

Compound 2 (5 mg, 1.8 μmol) was transferred to the FASTLAB™ chemistry synthesizer platform reaction vessel prior to elution of 4-[$^{18}$F]fluorobenzaldehyde is returned from the MCX+ cartridge. The mixture was then heated at 70° C. for 17 minutes). Analytical HPLC confirmed that the RCP of the Compound 3B product was 63±9%.

The crude reaction mixture was diluted with water (10 mL) and loaded onto preparative HPLC. A 10 mM ammonium acetate vs acetonitrile system gave complete separation between the 3 possible radioactive components of the crude reaction mixture, namely [$^{18}$F]fluoride (T$_R$=0.5 mins), [$^{18}$F]Compound 3B (T$_R$=6 mins) and 4-[$^{18}$F]fluorobenzaldehyde (T$_R$=9 mins). Recovery of radioactivity from the HPLC system was good, with a recovery efficiency of 97%. The purified product was obtained by collecting the around 6 mins retention time.

Example 5

HPLC Separation of $^{18}$F-Labelled c-Met Cyclic Peptide from Unlabelled Peptide Compound 3A was prepared according to Example 3.

(i) Analytical HPLC Conditions.

Column: XBridge Shield RP 18 (4.6 × 50) mm, 2.5 μm,
Aqueous mobile phase A: 10 mM NH$_4$Ac (buffer) pH ca. 6.8;
Organic mobile phase B: Acetonitrile.
Column temperature: 25° C.
Flow: 1.2 ml/min.

| Gradient: | | | | | | |
|---|---|---|---|---|---|---|
| Minutes | 0 | 1 | 16 | 19 | 22 | 22.1 | 26 |
| % B | 20 | 20 | 40 | 100 | 100 | 20 | 20 |

(ii) Preparative HPLC Conditions

Column: XBridge Shield RP 18 (10 × 100) mm, 5 μm.
Aqueous mobile phase A: 10 mM NH$_4$Ac (buffer) pH ca. 6.8;
Organic mobile phase B: Ethanol (90%) Mobile phase A (10%).
Column temperature: 25° C.
Flow: 4 ml/min.

| Gradient: | | | | | | |
|---|---|---|---|---|---|---|
| Minutes | 0 | 1 | 16 | 20 | 25 | 26 |
| % B | 15 | 15 | 40 | 100 | 100 | 15 |

(iii) Analytical and Preparative HPLC Results.

| Compound | Analytical HPLC Retention time (minutes) | Preparative HPLC Retention time (minutes) |
|---|---|---|
| aniline hydrochloride | 1.8 | 3 |
| fluorobenzaldehyde | 4.3 | 13 |
| Compound 2 | 4.8 | undefined |
| Peptide 1 | 5.1 | undefined |
| Compound 3A | 8.8 | 19 |

Example 6

Biodistribution of $^{18}$F-Labelled c-Met Peptide (Compound 3B) in Tumour-Bearing Nude Mice CD-1 male nude mice (ca. 20 g) were housed in individual ventilated cages, with ad libitum access to food and water.

HT-29 cells (ATCC, Cat. no. HTB-38) were grown in McCoy's 5a medium (Sigma # M8403) supplemented with 10% fetal bovine serum and penicillin/streptomycin. Cells were split 1:3 two times a week, at 70-80% confluent using 0.25% trypsin and incubated in 5% $CO_2$ at 37° C. The mice were injected s.c under light gas anaesthesia (Isoflurane) with the HT-29 cell suspension at one site (nape of the neck) with a nominal dose of $10^6$ cells per injections in a volume of 100 µl using a fine bore needle (25 G). The tumours were then allowed to develop for 20 days, or until at least 200 $mm^3$ in volume (for inclusion in the study).

After the 20 day growth time, animals were injected with Compound 3B (0.1 ml, 1-5 MBq/animal) as an intravenous bolus via the tail vein. At various times post injection animals were euthanised, dissected and the following organs and tissues removed:

The tumour uptake was 2.3% id/g at 2 minutes, peaking at 30 minutes (3.8% id/g) then decreasing over time to 1.9% id/g at 120 mins pi. The overall retention within the tumour was 83%. There was reasonably rapid blood clearance over time (initial 2 minute blood was 9.2% id/g decreasing to 0.81% id/g at 120 mins pi). Key background tissue (e.g. lungs and liver) followed the blood clearance profile over time, with uptake at 120 min p.i. of 1.1% id/g (liver) and 1.56% id/g (lungs).

Example 7

Receptor Blocking Study of Compound 3B in Tumour-Bearing Nude Mice

The study of Example 6 was repeated with co-injection of 100 and 1000-fold excess of the non-radioactive analogue, Compound 3A (~1.5 µg and 15 µg excess per animal), with animals dissected at 120 minutes post injection. All animals in this study had a similar bodyweight (range of 25 to 30 g). The data demonstrated that a statistically significant reduction ($p<0.01$) in tumour uptake of Compound 3B was achieved with 1000-fold excess unlabelled peptide (HT-29 tumour uptake fell from 1.9 to 1.1% id/g; a 40% reduction).

Example 8

Primate PET Imaging of Compound 3B

The biodistribution of Compound 3B in three female cynomolgus monkeys was measured by PET. Two tracer injections were performed at each occasion:
(a) tracer alone (Compound 3B) 3 MBq/kg (base line study);
(b) tracer 9 MBq/kg with co-injection of with 0.15 mg/kg of Compound 3A (blockade study) four hours after baseline injection.

The tracer was injected as a bolus dose in 1-3 mL followed by 1 mL saline.

Blood samples (0.2 ml) for radioactivity determination were taken at intervals out to 210 minutes after administration. In the dynamic studies regions of interest were drawn in bone, heart, kidney, lung, liver, and muscle. In the whole-body studies, regions of interest were drawn in bone, brain, colon, heart, kidney, lung, liver, muscle, pancreas, small bowel, spleen, and bladder. Time-activity data were generated expressed as standard uptake values (SUV).

Specific binding (~40%) was observed in rhesus monkey liver in vitro using frozen section autoradiography. Rhesus monkey muscle was not observed to have any specific binding. In vivo studies in cynomolgus monkey showed a rapid uptake in liver which was reduced by >40% after co-injection of 0.15 mg/kg of Compound 3A. No specific binding to muscle in vivo was observed.

Example 9

Effect of Cyclodextrin on the Biodistribution of Compound 3B

The biodistribution of Compound 3B and Compound 3B formulated with the solubiliser hydroxypropyl-β-cyclodextrin (HPCD) were compared. No significant differences were found.

Example 10

Fully Automated Synthesis of Compound 3B

The synthesis analogous to Example 4 was carried out, using Compound 2 dissolved up in buffer or aniline solution and loaded onto the FASTLAB™ chemistry synthesizer platform cassette for immediate use.

The table below summarises the amount of each of the main radiolabelled constituents, as calculated by radiochemical purity of analytical HPLC:

| | Product | Compound 1 precursor | Compound 2 precursor |
|---|---|---|---|
| T = 0 mins | Compound 3B | 63 ± 9% | 75 ± 3% |
| | [$^{18}$F]Fluorobenzaldehyde | 28 ± 15% | 20 ± 3% |
| T = 60 mins | Compound 3B | 76 ± 20% | 92 ± 2% |
| | [$^{18}$F]Fluorobenzaldehyde | 20 ± 15% | 2 ± 1% |

Example 11

Automated Synthesis of Compound 3B Using SPE Purification

The synthesis of Example 4 was carried out using a FastLab™: (GE Healthcare Ltd) automated synthesiser apparatus. The cassette was configured with reagents, syringes and SPE cartridges as shown in FIG. 1.

The QMA (quaternary methyl ammonium water treatment), MCX+ (mixed cation exchange) and C2 (low hydrophobicity) SPE cartridges were all obtained from Waters.

During the FASTLAB™ chemistry synthesizer platform sequence the cartridges were (in tandem) conditioned with Ethanol. Immediately prior to use, the cartridges were primed with dilute (0.2% phosphoric acid). The crude reaction mixture was diluted with 1% phosphoric acid and loaded onto the SPE. The SPE was washed with water before the product was eluted in 6 mL water (80% ethanol), and the radiochemical purity (RCP) analysed by analytical HPLC.

The results, based on the starting amount of $^{18}$F-fluoride used, were as follows:

| Starting Activity (MBq) | End of Synthesis Yield (%) | RCP |
|---|---|---|
| 493 | 21 | >99% |
| 750 | 25 | >99% |
| 1,000 | 26 | >99% |
| 49,000 | 19 | 94% |
| 61,000 | 18 | 98% |
| 67,400 | 21 | 96% |

Example 12

Formulation and Freeze-Drying of Precursor

The peptide precursor Compound 2 (2.5 or 5 mg) was mixed with a formulation buffer (disodium hydrogen phosphate dihydrate and citric acid monohydrate, pH 2.8) and stirred until a homogenous suspension was obtained. 13 mm vials from a FASTlab™; and automated synthesizer apparatus (GE Healthcare Ltd) with freeze-drying stoppers were each filled with 1 mL suspension. The vials were then frozen in the freeze-drying unit and subjected to a 4-day freeze-drying cycle.

All vials containing peptide gave satisfying lyophilised cakes. The lyophilised precursor was found to dissolve much more quickly than dry-dispensed Compound 2.

Example 13

Effect of pH on Solubility

Compound 3B was prepared on a FASTLAB™ synthesizer, and the product eluent (~6 mL) was collected in a vial containing 2 mL of formulation buffer (pABA, citric buffer, pH 7). A cloudy solution was observed. The solution (8 ml) was easily filtered through a pre-filter (Pall 25 mm filter with 0.2 μm Supor membrane with hydrophobic repel stripe, part no. 6124211), giving a clear solution.

The filtered solution was divided in to 4×2 mL samples and the pH in the 4 samples adjusted with phosphate (solid, so as not to change volume) as follows:

| | |
|---|---|
| Vial 1 | pH 7.5 (original solution, no adjustments) |
| Vial 2 | pH 6.1 |
| Vial 3 | pH 8.6 |
| Vial 4 | pH 9.1 |

All samples were stored in the dark at ambient temperature. To evaluate potential aggregation/precipitation, the 4 samples were followed by static light scattering for 28 days. The following was observed:

pH 6.1 showed visual precipitate at day 10;

no indication of aggregation at pH≥7.5 was observed after 28 days.

Example 14

Human Studies

Imaging with Compound 3B was studied in 6 human patients previously diagnosed with head and neck squamous cell carcinoma. The agent was well-tolerated (no adverse effects). 5 of the 6 patients had moderate/high uptake of the tracer, and 1 patient had low (similar to contralateral side). This is consistent with the literature reports of 80% of such patients overexpressing c-Met.

---

The invention claimed is:

1. An imaging agent composition which comprises (i) a $^{18}$F-radiolabelled c-Met binding cyclic peptide and (ii) an unlabelled c-Met binding cyclic peptide;
   wherein the unlabelled c-Met binding cyclic peptide has the same amino acid sequence as the radiolabelled c-Met binding cyclic peptide;
   wherein the unlabelled c-Met binding cyclic peptide is present in the composition at no more than 50 times the molar amount of the $^{18}$F-labelled c-Met binding cyclic peptide; and
   wherein the c-Met binding cyclic peptide is an 18 to 30-mer cyclic peptide of Formula I:

$$Z^1\text{-[cMBP]-}Z^2 \qquad (I)$$

where cMBP is of Formula II:

$$\text{-(A)}_x\text{-Q-(A')}_y\text{-} \qquad (II);$$

and Q is the amino acid sequence SEQ ID NO: 1:

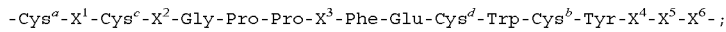

wherein $X^1$ is Asn, His, or Tyr;
   $X^2$ is Gly, Ser, Thr or Asn;
   $X^3$ is Thr or Arg;
   $X^4$ is Ala, Asp, Glu, Gly or Ser;
   $X^5$ is Ser or Thr;
   $X^6$ is Asp or Glu;
   and $\text{Cys}^{a-d}$ are each cysteine residues such that residues a and b as well as c and d are cyclised to form two separate disulfide bonds;
   A and A' are independently any amino acid other than Cys, with the proviso that at least one of A and A' is present and is Lys;
   x and y are independently integers of value 0 to 13, and are chosen such that [x+y]=1 to 13;
   $Z^1$ is attached to the N-terminus of cMBP, and is H or $M^{IG}$;
   $Z^2$ is attached to the C-terminus of cMBP and is OH, $OB^c$, or $M^{IG}$,
   where $B^c$ is a biocompatible cation;
   each $M^{IG}$ is independently a metabolism inhibiting group which is a biocompatible group which inhibits or suppresses in vivo metabolism of the cMBP; and
   wherein the labelled cMBP is labelled at the Lys residue of the A or A' groups with $^{18}$F, and
   wherein the unlabelled c-Met binding cyclic peptide excludes the c-Met binding cyclic peptide labelled with $^{19}$F, where said $^{19}$F labelled c-Met binding cyclic peptide and $^{18}$F-radiolabelled c-Met binding cyclic peptide differ only in the isotopes of the fluorine atom.

2. The imaging agent composition of claim 1, where cMBP is of Formula IIA:

$$\text{-(A)}_x\text{-Q-(A')}_z\text{-Lys-} \qquad (IIA)$$

wherein: z is an integer of value 0 to 2 and [x+z]=0 to 12, and cMBP comprises only one Lys residue.

3. The imaging agent composition of claim 1, wherein cMBP comprises the amino acid sequence of either SEQ ID NO: 2 or SEQ ID NO: 3:

(SEQ ID NO: 2)

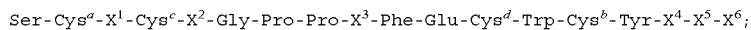

(SEQ ID NO: 3)

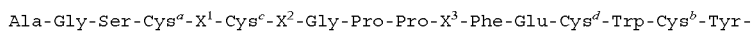

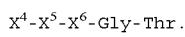

4. The imaging agent composition of claim 1, wherein $X^3$ is Arg.

5. The imaging agent composition of claim 1, wherein either the -(A)$_x$- or -(A')$_y$- groups comprise a linker peptide which is chosen from:

-Gly-Gly-Gly-Lys-, (SEQ ID NO: 4)

-Gly-Ser-Gly-Lys- (SEQ ID NO: 5)

or

-Gly-Ser-Gly-Ser-Lys-. (SEQ ID NO: 6)

6. The imaging agent composition of claim 5, where cMBP has the amino acid sequence (SEQ ID NO: 7):

Ala-Gly-Ser-Cys$^a$-Tyr-Cys$^c$-Ser-Gly-Pro-Pro-Arg-Phe-Glu-Cys$^d$-Trp-Cys$^b$-Tyr-Glu-Thr-Glu-Gly-Thr-Gly-Gly-Gly-Lys.

7. The imaging agent composition of claim 1, where both $Z^1$ and $Z^2$ are independently $M^{IG}$.

8. The imaging agent composition of claim 7, where $Z^1$ is acetyl and $Z^2$ is a primary amide.

9. The imaging agent composition of claim 1, wherein cMBP is labelled at epsilon amine group of the Lysine residue of the A or A' groups with $^{18}$F.

10. The imaging agent composition of claim 1, wherein cMBP is labelled at epsilon amine group of the carboxy terminal Lysine with $^{18}$F.

11. The imaging agent composition of claim 1, further comprising 4-aminobenzoic acid as radioprotectant and 5-10% v/v ethanol as solubilizer.

12. The imaging agent composition of claim 1, wherein the $^{18}$F-radiolabelled c-Met binding cyclic peptide has the following structure:

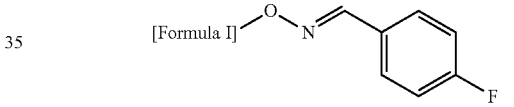

wherein n=18 and Formula I is radiolabelled at the Lysine residue of the A or A' groups of the cMBP.

13. The imaging agent composition of claim 1, wherein the $^{18}$F-radiolabelled c-Met binding cyclic peptide has the following structure:

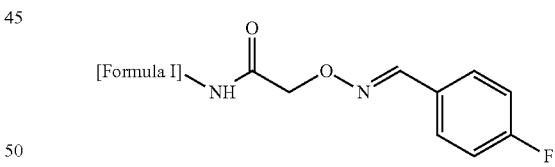

wherein n=18 and Formula I is radiolabelled at the Lysine residue of the A or A' groups of the cMBP.

14. The imaging agent composition of claim 1, which is maintained at or above pH 7.5 and/or further comprises a solubiliser.

15. The imaging agent composition of claim 1, which further comprises one or more radioprotectants.

16. A pharmaceutical composition which comprises the imaging agent composition of claim 1 together with a biocompatible carrier, in a sterile form suitable for mammalian administration.

* * * * *

SEQUENCE LISTING

```
<160> NUMBER OF SEQ ID NOS: 7

<210> SEQ ID NO 1
<211> LENGTH: 17
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (1)..(13)
<220> FEATURE:
<221> NAME/KEY: VARIANT
<222> LOCATION: (2)..(2)
<223> OTHER INFORMATION: N, H or Y
<220> FEATURE:
<221> NAME/KEY: DISULFID
<222> LOCATION: (3)..(11)
<220> FEATURE:
<221> NAME/KEY: VARIANT
<222> LOCATION: (4)..(4)
<223> OTHER INFORMATION: G, S, T or N
<220> FEATURE:
<221> NAME/KEY: VARIANT
<222> LOCATION: (8)..(8)
<223> OTHER INFORMATION: T or R
<220> FEATURE:
<221> NAME/KEY: VARIANT
<222> LOCATION: (15)..(15)
<223> OTHER INFORMATION: A, D, E, G or S
<220> FEATURE:
<221> NAME/KEY: VARIANT
<222> LOCATION: (16)..(16)
<223> OTHER INFORMATION: S or T
<220> FEATURE:
<221> NAME/KEY: VARIANT
<222> LOCATION: (17)..(17)
<223> OTHER INFORMATION: D or E

<400> SEQUENCE: 1

Cys Xaa Cys Xaa Gly Pro Pro Xaa Phe Glu Cys Trp Cys Tyr Xaa Xaa
```

```
1               5                  10                 15

Xaa

<210> SEQ ID NO 2
<211> LENGTH: 18
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (2)..(14)
<220> FEATURE:
<221> NAME/KEY: VARIANT
<222> LOCATION: (3)..(3)
<223> OTHER INFORMATION: N, H OR Y
<220> FEATURE:
<221> NAME/KEY: DISULFID
<222> LOCATION: (4)..(12)
<220> FEATURE:
<221> NAME/KEY: VARIANT
<222> LOCATION: (5)..(5)
<223> OTHER INFORMATION: G, S, T or N
<220> FEATURE:
<221> NAME/KEY: VARIANT
<222> LOCATION: (9)..(9)
<223> OTHER INFORMATION: T or R
<220> FEATURE:
<221> NAME/KEY: VARIANT
<222> LOCATION: (16)..(16)
<223> OTHER INFORMATION: A, D, E, G or S
<220> FEATURE:
<221> NAME/KEY: VARIANT
<222> LOCATION: (17)..(17)
<223> OTHER INFORMATION: S or T
<220> FEATURE:
<221> NAME/KEY: VARIANT
<222> LOCATION: (18)..(18)
<223> OTHER INFORMATION: D or E

<400> SEQUENCE: 2

Ser Cys Xaa Cys Xaa Gly Pro Pro Xaa Phe Glu Cys Trp Cys Tyr Xaa
1               5                  10                 15

Xaa Xaa

<210> SEQ ID NO 3
<211> LENGTH: 22
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (4)..(16)
<220> FEATURE:
<221> NAME/KEY: VARIANT
<222> LOCATION: (5)..(5)
<223> OTHER INFORMATION: N, H or Y
<220> FEATURE:
<221> NAME/KEY: DISULFID
<222> LOCATION: (6)..(14)
<220> FEATURE:
<221> NAME/KEY: VARIANT
<222> LOCATION: (7)..(7)
<223> OTHER INFORMATION: G, S, T or N
<220> FEATURE:
<221> NAME/KEY: VARIANT
<222> LOCATION: (11)..(11)
<223> OTHER INFORMATION: T or R
<220> FEATURE:
<221> NAME/KEY: VARIANT
<222> LOCATION: (18)..(18)
<223> OTHER INFORMATION: A, D, E, G or S
<220> FEATURE:
```

```
<221> NAME/KEY: VARIANT
<222> LOCATION: (19)..(19)
<223> OTHER INFORMATION: S or T
<220> FEATURE:
<221> NAME/KEY: VARIANT
<222> LOCATION: (20)..(20)
<223> OTHER INFORMATION: D or E

<400> SEQUENCE: 3

Ala Gly Ser Cys Xaa Cys Xaa Gly Pro Pro Xaa Phe Glu Cys Trp Cys
1               5                   10                  15

Tyr Xaa Xaa Xaa Gly Thr
            20

<210> SEQ ID NO 4
<211> LENGTH: 4
<212> TYPE: PRT
<213> ORGANISM: Artificial
<220> FEATURE:
<223> OTHER INFORMATION: synthetic peptide

<400> SEQUENCE: 4

Gly Gly Gly Lys
1

<210> SEQ ID NO 5
<211> LENGTH: 4
<212> TYPE: PRT
<213> ORGANISM: Artificial
<220> FEATURE:
<223> OTHER INFORMATION: synthetic peptide

<400> SEQUENCE: 5

Gly Ser Gly Lys
1

<210> SEQ ID NO 6
<211> LENGTH: 5
<212> TYPE: PRT
<213> ORGANISM: Artificial
<220> FEATURE:
<223> OTHER INFORMATION: synthetic peptide

<400> SEQUENCE: 6

Gly Ser Gly Ser Lys
1               5

<210> SEQ ID NO 7
<211> LENGTH: 26
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (4)..(16)
<220> FEATURE:
<221> NAME/KEY: DISULFID
<222> LOCATION: (6)..(14)

<400> SEQUENCE: 7

Ala Gly Ser Cys Tyr Cys Ser Gly Pro Pro Arg Phe Glu Cys Trp Cys
1               5                   10                  15

Tyr Glu Thr Glu Gly Thr Gly Gly Gly Lys
            20                  25
```